US011246849B2

(12) United States Patent
Wakayama et al.

(10) Patent No.: US 11,246,849 B2
(45) Date of Patent: Feb. 15, 2022

(54) NERVE GROWTH PROMOTER

(71) Applicant: LAIMU CORPORATION, Yokohama (JP)

(72) Inventors: Sachio Wakayama, Yokohama (JP); Akihiro Tai, Shobara (JP); Takeru Koga, Shobara (JP)

(73) Assignee: LAIMU CORPORATION, Yokohama (JP)

( * ) Notice: Subject to any disclaimer, the term of this patent is extended or adjusted under 35 U.S.C. 154(b) by 721 days.

(21) Appl. No.: 16/081,097

(22) PCT Filed: Jun. 5, 2018

(86) PCT No.: PCT/JP2018/021555
§ 371 (c)(1),
(2) Date: Aug. 30, 2018

(87) PCT Pub. No.: WO2018/225730
PCT Pub. Date: Dec. 13, 2018

(65) Prior Publication Data
US 2021/0205249 A1 Jul. 8, 2021

(30) Foreign Application Priority Data
Jun. 6, 2017 (JP) .............................. JP2017-112016

(51) Int. Cl.
*A61K 31/198* (2006.01)

(52) U.S. Cl.
CPC .................................. *A61K 31/198* (2013.01)

(58) Field of Classification Search
CPC .................................................. A61K 31/198
See application file for complete search history.

(56) References Cited

U.S. PATENT DOCUMENTS

| | | | |
|---|---|---|---|
| 6,294,520 B1 * | 9/2001 | Naito | A61K 8/44 514/1.2 |
| 2005/0131212 A1 | 6/2005 | Sieg et al. | |
| 2015/0126604 A1 | 5/2015 | Abel et al. | |

FOREIGN PATENT DOCUMENTS

| | | |
|---|---|---|
| JP | 61-501564 A | 7/1986 |
| JP | 04-091034 A | 3/1992 |
| JP | 2004-123564 A | 4/2004 |
| JP | 2016-515403 A | 5/2016 |
| JP | 2016-210720 A | 12/2016 |
| JP | 2017-141207 A | 8/2017 |
| WO | 1985/003869 A1 | 9/1985 |
| WO | 2006/079036 A2 | 7/2006 |
| WO | 2014/172580 A1 | 10/2014 |
| WO | 2018/047980 A1 | 3/2018 |

OTHER PUBLICATIONS

Shiraki et al. CAS:161:139487, 2014.*
Boebel et al. CAS: 97:214757, 1982.*
Extended European Search Report dated Jan. 28, 2021 issued in the corresponding European patent application No. 18813903.4.
International Preliminary Report on Patentability for PCT/2018/021555, dated Dec. 10, 2019.
Yutaro Obara et al., "The Signaling Pathway of Neurotrophic Factor Biosynthesis", Drug News Perspect, 15, 290-298 (2002).
S. Korsching et al., "Levels of nerve growth factor and its mRNA in the cellral nervous system of the rat correlate with cholinergic innervation", The EMBO Journal, 4, 1389, (1985).
Hans Thoenen et al., "The Physiological Function of Nerve Growth Factor in the Central Nervous System Comparison With the Periphery", Reviews of Physiology, Biochemistry and Pharmacology, 109, 145 (1987).
Franz Hefti, "Chronic Administration of Nerve Growth Factor andvOther Neurotrophic Factors to the Brain", Neurobiology of Aging, 9, 689-690 (1988).
David Hepler et al., "Lesions in Nucleus Basalis Magnocellularis and Medial Septal Area of Rats Produce Qualitatively Similar Memory Impairments", Journal of Neuroscience, 5, 866 (1985).
Elliott J. Mufson, et al., "Loss of Nucleus Basalis Neurons Containing trkA Immunoreactivity in Individuals With Mild Cognitive Impairment and Early Alzheimer's Disease", Journal of Comparative Neurology, 427, 19-30 (2000).
Coelho, C.N.D.et al., "Methionine and neural tube closure in cultured rat embryos:morphological and biochemical analyses", Teratology, vol. 42 p. 437-451 (1990).
International Search Report and Written Opinion of PCT/JP2018/021555 dated Aug. 21, 2018.
Office Action dated Dec. 21, 2021, issued in the corresponding Japanese Patent application No. 2018-102184 with its English Machine Translation.

* cited by examiner

*Primary Examiner* — Rei Tsang Shiao
(74) *Attorney, Agent, or Firm* — Browdy and Neimark, PLLC

(57) ABSTRACT

The nerve growth promoter of the invention contains a valine in which the hydrogen atom of the amino group may be substituted with a substituent. The nerve growth promoter of the invention has a high effect of promoting differentiation of stem cells into nerve cells and formation of neurites in nerve cells, and the active ingredient therein is hardly degraded by digestive enzymes.

19 Claims, 4 Drawing Sheets

NERVE GROWTH PROMOTER

TECHNICAL FIELD

The present invention relates to a nerve growth promoter.

BACKGROUND ART

Signaling in a human brain is attained in a network where nerve cells conjugate via a synapse in the form of a net. However, in an adult, 100,000 or more such nerve cells disappear a day, which is said to be a cause of central nervous system diseases such as Alzheimer's dementia. Consequently, it is said to be necessary to ascertain the causes of the diseases of this type and to establish medical treatment and prevention of these diseases.

The cause of Alzheimer's dementia is not as yet completely ascertained, but a hypothesis that a causal substance thereof would be β-amyloid is widely accepted. When β-amyloid agglutinates inside a brain, it is deposited to form amyloid plaque, and thereafter nerve cells die. Consequently, many of the previous studies are to propose an inhibitor against a β-amyloidogenic enzyme, β-secretase or γ-secretase, or to propose immunotherapy using an antigen or antibody such as amyloid. However, various problems have been pointed out in that these inhibitors and therapy could not attain a sufficient effect, or may lead to side effects.

On the other hand, an investigation of applying neurotrophin to a therapeutic agent for Alzheimer's disease is under way. Neurotrophin is a general term for a substance that promotes the life, differentiation and regeneration of nerve cells, and various neurotrophic factors have been identified (for example, see NPL 1). Above all, a nerve growth factor (NGF) is a neurotrophin for basal fore-brain cholinergic neuron. (BFCN) relating to the clinical condition of Alzheimer's disease and has therefore attracted attention, and studies about it are now being made actively (for example, see NPLs 2 and 3). Specifically, Alzheimer's disease is an unexplained disorder of dementia, for which there is no effective treatment, but it is known that in a patient's brain, there has occurred remarkable failures in BFCN (decrease in the number of the cells, atrophia of cell bodies, denaturation of neurites). With that, BFCN is a nerve path relating to memory and learning performance, and the dementia condition of Alzheimer's disease well corresponds to the disorder of the nerve path. Consequently, one cause of Alzheimer's disease has become considered to be a deficiency of NGF, and applying a neurotrophin to a remedy for Alzheimer's disease has become tried. For example, there have been made some reports that, when NGF is administered to a model animal that has been modified to induce death of BFCN therein, neuronal death is prevented (for example, see NPLs 4 and 5). In addition, there has also been made a report that, in a mild cognitive impairment (MCI) patient or in an early Alzheimer's disease patient, the number of NGF acceptor (TrkA) immunopositive cells in the base of forebrain has a correlation to the result of a cognitive functioning test (see NPL 6).

CITATION LIST

Non-Patent Literature

NPL 1: Drug News Perspect, 15, 290-298 (2002)
NPL 2: The EMBO Journal, 4, 1389, (1985)
NPL 3: Reviews of Physiology, Biochemistry and Pharmacology, 109, 145 (1987)
NPL 4: Neurobiology of Aging, 9, 689-690 (1988)
NPL 5: Journal of Neuroscience, 5, 866 (1985)
NPL 6: Journal of Comparative Neurology, 427, 19-30 (2000)

SUMMARY OF INVENTION

Technical Problem

As described above, an attempt to apply NGF to a remedy for Alzheimer's disease has been being made. However, NGF is a high-molecular protein and is degraded by protease in the digestive tract, and therefore even though taken orally, NGF could not reach a brain. In addition, even when given intravenously, NGF could not mass through a blood-brain barrier and therefore could not reach a brain. Consequently, for externally administering NGF so as to make the neural differentiation promoting action and the nerve growth promoting action thereof expressed in a brain, there would be only one way to directly administer NGF in the brain parenchyma or in the brain ventricle, which, however, is problematic as greatly increasing the burden on patients.

Given the situation and for the purpose of solving the problems in the conventional art, the present inventors have continued further investigations in an attempt to provide a medication, which has a neural differentiation promoting effect and a neurite formation effect, and in which the active ingredient is hardy degraded by digestive enzymes and can pass through a blood-brain barrier.

Solution to Problem

For the purpose of solving the above-mentioned problems, the present inventors have focused attention on an amino acid as a low-molecular compound that could be expected to have physiological activity and enzyme resistance, and have investigated the action thereof on nerve cells, and as a result, have found that, in particular, valine has an effect of neurite formation and a neural differentiation promoting effect, and is therefore useful as a nerve growth promoter. The present invention has been proposed on the basis of these findings, and specifically has the following constitution.

[1] A nerve growth promoter containing a valine in which the hydrogen atom of the amino group may be substituted with a substituent.
[2] The nerve growth promoter according to [1], further containing a methionine in which the hydrogen atom of the amino group play be substituted with a substituent.

Advantageous Effects of Invention

A valine far use in the present invention has an effect of neurite formation and an effect of promoting differentiation of stem cells into nerve cells, and is useful as a nerve growth promoter. In addition, a valine is a low-molecular compound and is therefore hardly degraded by digestive enzyme and can pass through a blood-brain harrier. Consequently, the nerve growth promoter containing a valine is such that, for example, even when taken orally, the valine therein can reach a brain while maintaining the structure thereof and can express the activity thereof in the brain.

DESCRIPTION OF EMBODIMENTS

Figure 1:
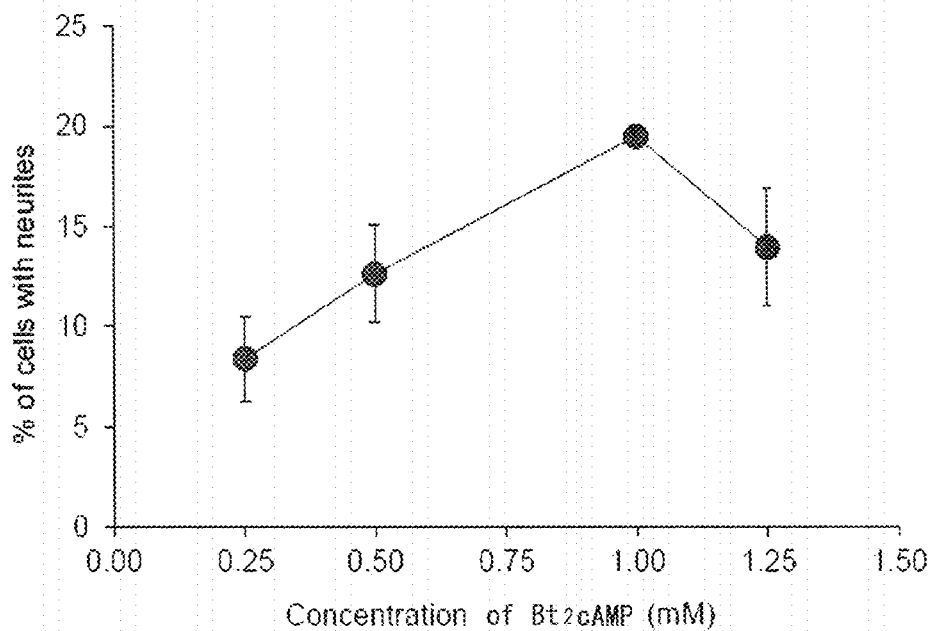
FIG. 1 This is a graph showing the $Bt_2cAMP$ concentration dependency of a neurite formation rate in PC12 cells.

The present invention is described in detail hereinunder. The description of the constitutive elements of the invention given hereinunder is for some typical embodiments or examples of the invention, to which, however, the invention should not be limited. In this description, the numerical range expressed by the wording "a number to another number" means the range that falls between the former number indicating the lower limit of the range and the latter number indicating the upper limit thereof.

The nerve growth promoter of the present invention is characterized by containing a valine in which the hydrogen atom of the amino group may be substituted with a substituent. In the following description, a valine in which the hydrogen atom of the amino group is substituted with a substituent may be referred to as "an N-substituted valine", and an N-substituted valine and an unsubstituted amine may be collectively referred to as "an N-substituted or unsubstituted valine".

A valine is a compound represented by the following formula and is an α-amino acid in which an amino group bonds to the α-positioned carbon, and is a branched-chain amino acid (BCAA) having a branched structure.

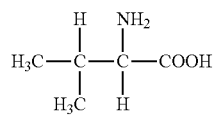

A valine is one of human essential amino acids, and is known to be utilized as an energy source in a living body and have an effect of promoting protein synthesis in skeletal muscles and inhibiting protein degradation. On the other hand, the present inventors further investigated the physiological activity of a valine and recognized an effect of promoting differentiation of stem cells into nerve cells (neural differentiation promoting effect) and an effect of neurite formation (neurite forming effect) of a valine, and have therefore clarified that a valine can exhibit an excellent function as a nerve growth promoter. Human digestive enzymes include, as roughly classified so, a carbohydrate-degrading enzyme, a protein-degrading enzyme and a lipolytic enzyme, but a valine is not degraded by any of these enzymes and could be absorbed by the gastrointestinal tract while having the structure thereof as it is. In addition, a valine having been absorbed by the gastrointestinal tract and moved into the bloodstream can pass through the blood-brain barrier. Consequently, a nerve growth promoter containing a valine can reach a brain, for example, even though taken orally, while having the structure thereof as it is, and can effectively express the effect thereof in the brain.

An N-substituted or unsubstituted valine for use in the present invention is preferably a free amino acid. In the case where a valine exists as a structural unit of a protein or a peptide, the valine is in a form where the amino group thereof undergoes dehydrating condensation with a carboxyl group of another amino acid to form a peptide bond and the carboxyl group further undergoes dehydrating condensation with the amino group of still another amino acid to form a peptide bond.

An N-substituted or unsubstituted valine may be an L-form or a D-form, and may be contained in the nerve growth promoter as a mixture of an L-form and a D-form, but preferably, more than 50 mol % of the total amount of an N-substituted or unsubstituted valine that the nerve growth promoter contains is an L-form, more preferably more than 70 mol % thereof is an L-form, even more preferably more than 80 mol % thereof is an L-form, and most preferably all the N-substituted or unsubstituted value that the nerve growth promoter contains is an L-form.

The N-substituted or unsubstituted valine for use in the present invention may be a synthesized one or one extracted from a natural source. A valine synthesis method includes a method of reacting α-bromoisobutyric acid and ammonia, a synthesis method using Strecker reaction, and a synthesis method through amino acid fermentation using microorganisms. For valine extraction from a natural source, mechanical fragmentation or homogenization of a natural source, hydrolysis with enzyme, acid or base, and various separation purification methods may be employed.

Regarding the N-substituted valine for use in the present invention, one or two of the two hydrogen atoms constituting the amino group may be substituted each with a substituent, but preferably one hydrogen atom is substituted. When the two hydrogen atoms of the amino group are substituted with substituents, the two substituents may be the same as or different from each other. The type of the substituent is not specifically limited, and examples thereof include an alkyl group and an acyl group. The carbon number of the alkyl group is preferably 1 to 10, more preferably 1 to 6, and may be selected from a range of, for example, 1 to 3. The carbon number of the acyl group is preferably 2 to 10, more preferably 2 to 6, and may be selected from a range of, for example, 1 to 3. An acetyl group or the like may be employed.

In the following, a specific example of a valine in which the hydrogen atom of the amino group is substituted with a substituent (N-substituted valine) is exemplified. However, the N-substituted valine usable in the present invention should not be limitatively interpreted by the specific example.

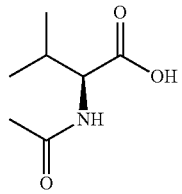

N-acetyl-L-valine

The valine in the nerve growth promoter of the present invention may be composed of an unsubstituted valine alone, or may be composed of an N-substituted valine alone, or may contain both an unsubstituted valine and an N-substituted valine. In the case where the nerve growth promoter contains an N-substituted valine, the N-substituted valine may be all the same or may be a combination of two or more kinds of N-substituted valines.

The nerve growth promoter of the present invention may be composed of an N-substituted or unsubstituted valine alone, or may contain any other component (additional component) than an N-substituted or unsubstituted valine. Preferred examples of the other component usable in the nerve growth promoter include a methionine. When a methionine is used as combined with an N-substituted or unsubstituted valine, the nerve growth promoting effect of the promoter can be enhanced more as compared with the case using an N-substituted or unsubstituted valine alone. A methionine is a compound represented by the following formula, and may be an L-form or a D-form, and the nerve growth promoter may contain a mixture of an L-form and a D-form of a methionine.

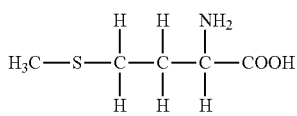

In the methionine to be combined with an N-substituted or unsubstituted valine, the hydrogen atom of the amino group may be substituted with a substituent, but from the viewpoint of enhancing the nerve growth promoting effect, the methionine is preferably unsubstituted. More preferably, an unsubstituted methionine and an unsubstituted valine are combined and used in the present invention. Here, in the methionine in which the amino group is substituted with a substituent (hereinafter this may referred to as "N-substituted methionine"), one or two of the two hydrogen atoms constituting the amino group may be substituted each with a substituent, hut preferably, one hydrogen atom is substituted. When two hydrogen atoms of the amino group are substituted with substituents, the two substituents may be the same or different mutually. Regarding the preferred range and the specific examples of the substituent, the preferred range and the specific examples of the substituent, with which the hydrogen atom of the amino group is substituted in the N-substituted valine mentioned above, may be referred to.

In the following, a specific example of a methionine in which the hydrogen atom of the amino group is substituted with a substituent (N-substituted methionine) is exemplified. However, the N-substituted methionine usable in the present invention should not be limitatively interpreted by the specific example.

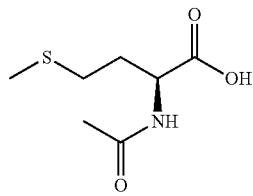

N-acetyl-L-methionine

In the case where the nerve growth promoter of the present invention contains a valine and a methionine (in both of these, the hydrogen atom of the amino group may be substituted with a substituent), preferably, the content of the valine is 1% by weight or more relative to the total amount of the valine and the methionine, more preferably 10% by weight or more, even more preferably 30% by weight or more. Also preferably, the valine content is 99% by weight or less, more preferably 90% by weight or less, even more preferably 70% by weight or less.

In the case where the N-substituted or unsubstituted valine in the nerve growth promoter of the present invention is one, for example, extracted from a natural source, the nerve growth promoter may contain any other natural source-derived components than the N-substituted or unsubstituted valine. In addition, the nerve growth promoter of the present invention may contain any other various components than the N-substituted or unsubstituted. For example, in the case where the nerve growth promoter contains a vehicle, its shapability may be bettered and, in addition, the amount of the nerve growth promoter may be increased without changing content of N-substituted or unsubstituted valine therein, or the handleability thereof may be bettered. Not specifically limited, dextrin is preferred for the vehicle. The dilution magnification with the vehicle is preferably 2 to 10 times by mass, more preferably 2 to 7 times, even more preferably 3 to 5 times.

In the case where the nerve growth promoter contains any other component than the N-substituted or unsubstituted valine, the content of the N-substituted or unsubstituted valine in the nerve growth promoter is preferably 0.01% by mass or more relative to the total mass of the nerve growth promoter, more preferably 0.1% by mass or more, even more preferably 1% by mass or more. For example, the content may be 50% by mass or more, 90% by mass or more, or 99% by mass or more.

The nerve growth promoter of the present invention has an effect of promoting differentiation of stem cells into nerve cells (neural differentiation promoting effect), and an effect of forming neurites in nerve cells (neurite formation effect), and in particular, can effectively promote formation of neurites induced by dibutyryl cAMP (Bt$_2$cAMP: dibutyryladenosine 3',5'-cyclic monophosphate), and neural differentiation induced by a nerve growth factor (NGF).

Consequently, the case where the nerve growth promoter of the present invention is taken orally and where the components thereof are absorbed by the gastrointestinal tract, it can effectively promote differentiation of stem cells into nerve cells and formation of neurites in the nerve systems that it has reached irrespective of peripheral nerves or central nerves, and can contribute toward reconstruction of nerve circuits that have been damaged by denaturation or damage of neurites therein. As a result, damages of cognition function and motor function caused by neurodegenerative disorders or nerve damages can be thereby effectively relieved. Here, the nerve growth promoter of the present invention uses a valine or an N-substituted valine of a valine derivative that is a biogenic substance, and is therefore highly safe, and in addition, since valine and many N-substituted valines are not degraded by digestive enzymes, another advantage of the nerve growth promoter is that it can be readily used as an internal agent that can be taken orally.

In addition, the nerve growth promoter of the present invention has an effect of differentiation of stem cells cultivated in a medium into nerve cells. Consequently, the nerve growth promoter of the present invention can be effectively used as a differentiation promoter that promotes differentiation of stem cells into nerve cells in the field of regenerative medicine that utilizes pluripotent stem cells and neural precursor cells such as iPS cells. Accordingly, efficient production of nerve cells from stem cells has become possible, and the present invention can remarkably contribute toward increased production efficiency and cost reduction in various industries relating to regenerative medicine.

The amount to be used of the nerve growth promoter of the present invention may vary depending on the targeted disorders, but for example, the dose thereof is preferably as follows.

For example, in the case where the nerve growth promoter of the present invention is orally taken as an internal remedy, the dose thereof is preferably 80 to 2000 mg/adult standard body weight/day, and suitably, the dose is divided into 2 or 3 portions to be separately administered a day.

In the case where the nerve growth promoter of the present invention is added to a medium where pluripotent stem cells or neural precursor cells are cultivated, the amount to be added thereto is preferably 0.1% by mass or more as a ratio by mass relative to the total amount of the medium, more preferably 0.2% by mass or more, even more preferably 0.2 to 1.0% by mass. The amount of the N-substituted or unsubstituted valine to be added in the case is preferably 0.03% by mass or more as a dry weight thereof, more preferably 0.05% by mass or more, and even more preferably 0.05 to 0.25% by mass.

[Use of Nerve Growth Promoter]

As described above, the nerve growth promoter of the present invention has a nerve growth promoting effect and has an effect of promoting differentiation of stem cells such as pluripotent stem cells or neural precursors into nerve cells.

Consequently, the nerve growth promoter of the present invention can be effectively used as an internal preparation which is administered to animals such as human beings (patient) to relieve functional disorders thereof caused by neurodegenerative disorders or nerve damages. The growth promoter as an internal preparation may optionally contain any other various components than the above-mentioned valine or valine derivative and vehicle. For example, vitamins, vegetable powders, minerals, yeast extracts, colorants and tackifiers may be optionally added thereto. The kind of these components is not specifically limited, and the content thereof may be appropriately controlled within a range capable of sufficiently exhibiting the intended function.

In the regenerative medicine area utilizing pluripotent stem cells such as iPS cells or neural precursors, the nerve growth promoter of the present invention may be added to a diluent for a medium or cells and can be favorably used as a differentiation promoter promoting differentiation of such stem cells into nerve cells. The medium to which the nerve growth promoter is added may be any of liquid (bouillon) media, semi-fluid media, and solid (agar) media, and the composition thereof is not specifically limited. The diluent may be a one ordinary used in the art as a diluent for cells, such as a physiological saline solution, and the nerve growth promoter of present elation is applicable to any of them.

EXAMPLES

The present invention is described more specifically with reference to Examples given below. The materials, the ratio thereof and the operations in the following Examples may be appropriately varied not overstepping the scope and the spirit of the present invention. Accordingly, the range of the present invention should not be interpreted limitatively by the specific examples shown below.

[Preparation of Nerve Growth Promoter Solution]

In the manner mentioned below, a solution of L-valine (nerve growth promoter 1), an L-leucine solution and an L-isoleucine solution were prepared. The structure of each amino acid is shown below. As shown below, L-leucine and L-isoleucine are a branched chain amino acid having a branched structure like L-valine.

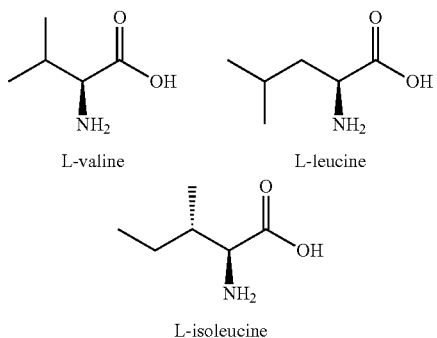

Preparation Example 1 Preparation of L-Valine Solution Using RPMI-1640

L-valine was dissolved in a medium (manufactured by Sigma Aldrich Corporation, RPMI-1640) to prepare an L-valine solution of 0.4 µg/mL and an L-valine solution of 4 µg/mL.

Preparation Example 2 Preparation of L-Valine Solution Using Nutrient Mixture F-12 Ham L-valine was dissolved in a medium (manufactured by Sigma Aldrich Corporation, Nutrient Mixture F-12 Ham) to prepare an L-valine solution of 0.4 µg/mL.

Comparative Preparation Example 1 Preparation of L-Leucine Solution L-Isoleucine Solution Using RPMI-1640

In the same manner as in Preparation Example 1 except that L-leucine or L-isoleucine was used in place of L-valine, an L-leucine solution of 0.4 µg/mL and an L-leucine solution of 4 µg/mL, as well as an L-isoleucine solution of 0.4 µg/mL, and an L-isoleucine solution of 4 µg/mL were prepared.

Comparative Preparation Example 2 Preparation of L-Leucine Solution L-Isoleucine Solution Using Nutrient Mixture F-12 Ham In the same manner as in Preparation Example 2 except that L-leucine or L-isoleucine was used in place of L-valine, an L-leucine solution of 0.4 µg/mL and an L-isoleucine solution of 0.4 µg/mL were prepared.

[Evaluation of Neurite Formation Effect and Neural Differentiation Promoting Effect]

Using rat adrenal medullary pheochromocytoma-derived PC12 cells obtained from Riken BioResource Research Center as a model, the L-valine solutions prepared in Preparation Examples were evaluated for the neurite formation effect and the neural differential promoting effect thereof. When acted on by $Bt_2cAMP$ (dibutyryladenosine 3',5'-cyclic monophosphate) or NGF, the PC12 cells are known to stop growing and to grow nerve fibers and elongate sympathetic ganglionic neuron-like dendrites. Here, L-valine was introduced into the $Bt_2cAMP$-inductive neurite formation process and the NGF-inductive neural differentiation process to thereby evaluate the neurite formation effect and the neural differentiation promoting effect thereof, and the effect of L-valine was compared with that of L-leucine and L-isolencine.

Here, the PC12 cells were cultivated using an RPMI-1640 medium containing 10% equine serum (inactivated), 5% bovine fetal serum (inactivated), 100 U/mL penicillin G and 100 µg/mL streptomycin, in a 5% $CO_2$ vapor phase in an incubator at 37° C., and the resultant cells in an about 70% confluent state were peeled with a basal medium and used in the experiment. In the following, the medium having the same composition as the medium used in cultivation of the PC12 cells is referred to as "basal medium".

(a) Investigation of Concentration of $Bt_2cAMP$ Added to Medium

As a preliminary experiment, $Bt_2cAMP$ to be added to the medium the following experiment (b) was investigated for the proper concentration thereof.

First, PC12 cells were floated in a basal medium and well suspended therein to be single cells. The suspension of PC12 cells was sown in a collagen-coated 96-well plate at $4.0 \times 10^3$ cells/95 µL/well, and cultivated therein in a 5% $CO_2$ vapor phase at 37° C. for 24 hours. After the cultivation, different types of Dulbecco PBS(<) (Dulbecco's phosphate buffered saline (free from Ca and Mg)) containing 5 mM, 10 mM, 20 mM or 25 mM of $Bt_2cAMP$ were separately added thereto in an amount of 5 µL/well such that the $Bt_2cAMP$ concentration becomes 0.25 mM, 0.5 mM, 1.0 mM or 1.25 mM, and the cells were further cultivated for 24 hours. After the cultivation, the medium was removed from each well, and a phosphate buffer (0.1 M, pH 7.2) containing 1% glutaraldehyde was added to each well in an amount of 100 µL/well, then statically left as it was for 20 minutes to fix the cells. Subsequently, the glutaraldehyde-containing phosphate buffer was removed from each well, and a Giemsa stain solution was added thereto in an amount of 100 µL/well and statically left as such for 2 to 3 minutes for staining. After the staining, the Giemsa stain solution was removed from each well, and the stained sample in the each well was washed two times with ultrapure water, and then dried.

Thus processed as above, the sample in each well was observed with a microscope, and the cells each having neurites in a length of two times or more the long-side diameter of the cell body were judged as positive, the percentage of the number of the positive cells to the number of all the cells (the number of all the cells judged for positivity or negativity) was calculated as a neurite formation rate. Here, for the judgement of positivity or negativity, 300 to 400 cells/well were observed.

In the same manner as above except that, in place of the $Bt_2cAMP$-containing Dulbecco PBS(−), a $Bt_2cAMP$-free Dulbecco PBS(−) was added to a medium in each well in an amount of 5 µL/well, PC12 cells were cultivated, fixed with glutaraldehyde and stained with a Giemsa solution, and the stained sample was observed to determine the neurite formation rate.

FIG. 1 shows the $Bt_2cAMP$ concentration dependency of the neurite formation rate. In FIG. 1, the neurite formation rate is expressed as ±SD, and SD is a standard deviation of the three experiments carried out in the same manner. The same shall apply to the expression of the neurite formation rate in FIGS. 2, 3 and 4 each showing the data in the following experiment (b).

As known from FIG. 1, the neurite formation rate was 19.5% and was the maximum when the $Bt_2cAMP$ concentration in the medium was 1.0 mM. In the following experiment (b), $Bt_2cAMP$ was used as an inducer for neurite formation, and therefore a concentration (0.5 mM) of ½ of the concentration (1.0 mM) at which the neurite formation rate could be the maximum was employed as the $Bt_2cAMP$ concentration in the medium.

(b) Evaluation of $Bt_2cAMP$-Inductive Neurite Formation Effect

In the same manner as in the above-mentioned preliminary experiment, a suspension of PC12 cells was sown in a collagen-coated 96-well plate at $4.0 \times 10^3$ cells/90 µL/well, and cultivated therein in a 5% $CO_2$ vapor phase at 37° C. for 24 hours. After the cultivation, Dulbecco PBS(−) containing 10 mM $Bt_2cAMP$, and the L-valine solution prepared in Preparation Example 1 or Preparation Example 2 were added to each well each in an amount of 5 µL/well, and the cells were further cultivated for 24 hours. At this time, the $Bt_2cAMP$ concentration in the medium in each well was 0.5 mM. Subsequently, in the same manner as in the above-mentioned preliminary experiment, the cells were fixed with glutaraldehyde and stained with Giemsa, and the stained sample was observed to determine the neurite formation rate.

In the same manner as above except that, in place of the L-valine solution in the above, the L-leucine solution or the L-isoleucine solution prepared in Comparative Preparation Example 1 or 2 was added to a medium in each well each in an amount of 5 µL/well, PC12 cells were cultivated, fixed with glutaraldehyde and stained with Giemsa, and the stained sample was observed to determine the neurite formation rate.

Figure 2:
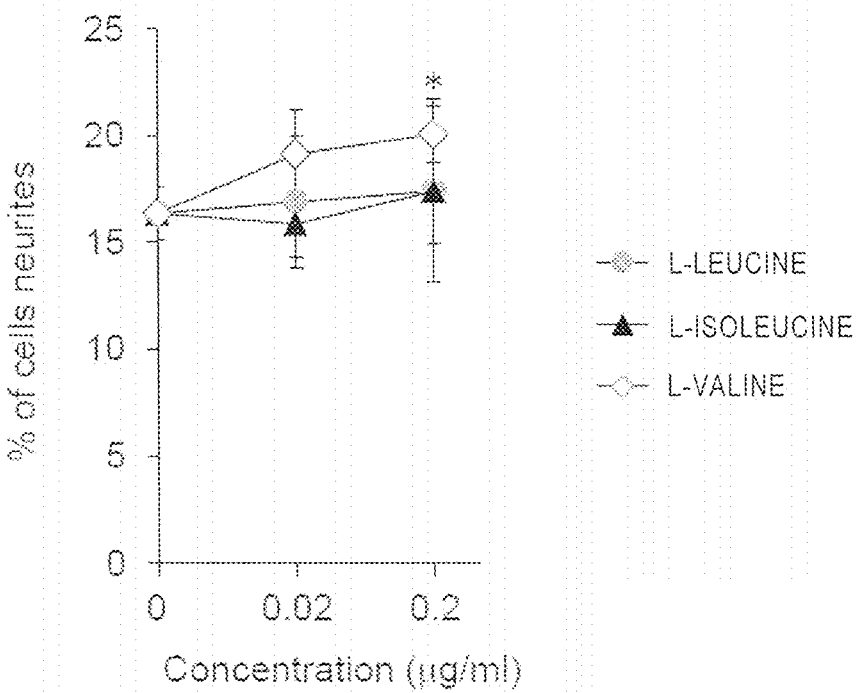
FIG. 2 This is a graph showing a neurite formation rate in cultivation of Bt$_2$cAMP-added PC12 cells in an RPMI-1640 medium added with an L-valine solution, an L-leucine solution or an L-isoleucine solution in an amount of 0.02 μg/mL or 0.2 μg/mL.
Figure 3:
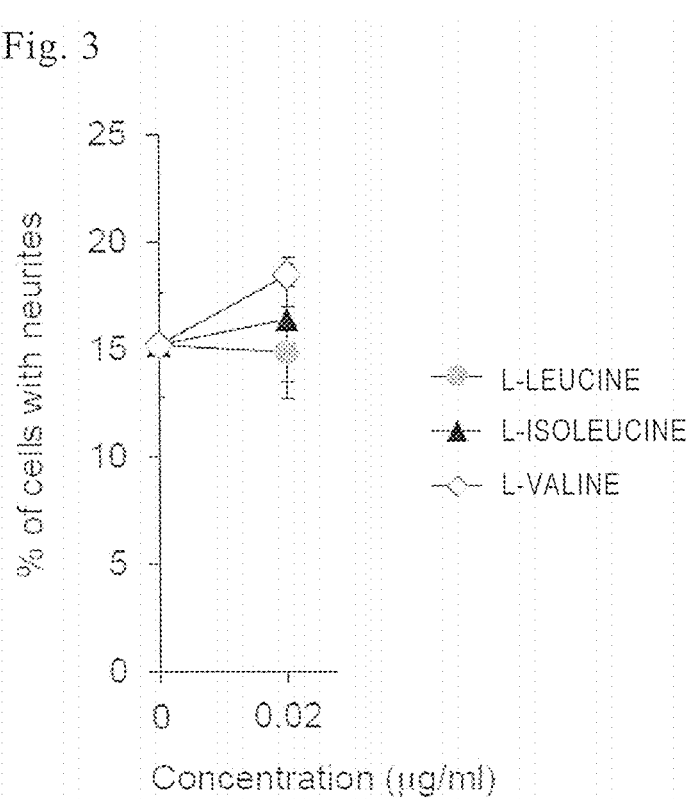
FIG. 3 This is a graph showing a neurite formation rate in cultivation of Bt$_2$cAMP-added PC12 cells in a Nutrient Mixture F-12 Ham medium added with an L-valine solution, an L-leucine solution or an L-isoleucine solution in an amount of 0.02 μg/mL.

FIG. 2 and FIG. 3 each show a neurite formation rate of each sample plotted relative to the amino acid concentration added to an RPMI-1640 medium or a Nutrient Mixture F-12 Ham medium. FIG. 2 shows a graph using the solutions prepared in Preparation Example 1 and Comparative Preparation Example 1 (solutions prepared by dissolving each branched chain amino acid in an RPMI-1640 medium); and FIG. 3 shows a graph using the solutions prepared in Preparation Example 2 and Comparative Preparation Example 2 (solutions prepared by dissolving each branched chain amino acid in a Nutrient Mixture F-12 Ham medium).

From FIGS. 2 and 3, it is known that, by adding a minor amount of L-valine to a medium, the neurite formation is significantly promoted. On the other hand, in the system where L-leucine or L-isoleucine was added to a medium, such a neurite formation promoting effect could not be recognized. This suggests that the neurite formation effect of a valine is not caused by a branched chain amino acid but is an effect peculiar to a valine.

Figure 4:
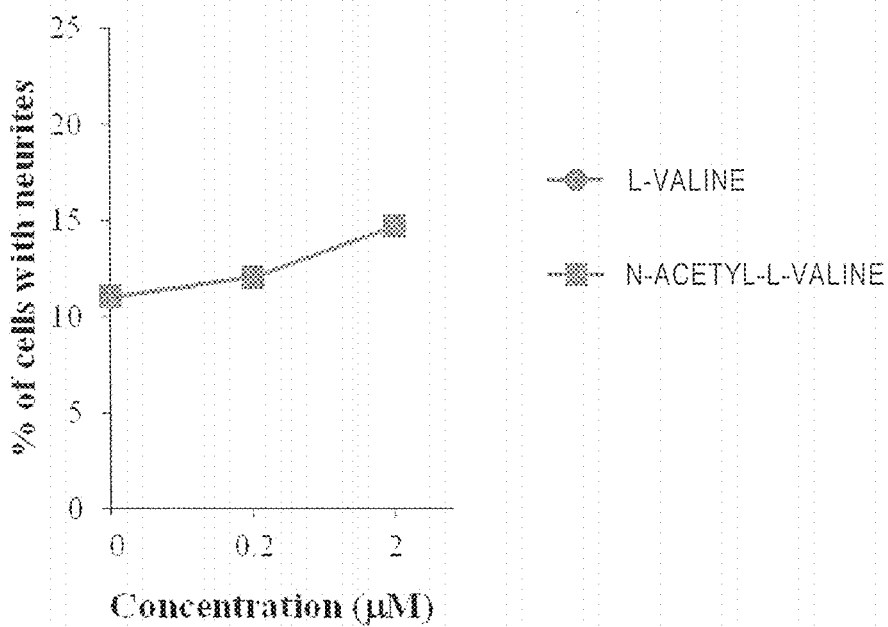
FIG. 4 This is a graph showing a neurite formation rate in cultivation of Bt$_2$cAMP-added PC12 cells in an RPMI-1640 medium added with an L-valine solution or an N-acetyl-L-valine solution in an amount of 0.2 μM, or 2 μM.

In addition, D-valine and N-acetyl-L-valine were evaluated for the effect of $Bt_2cAMP$-inductive neurite formation thereof in the same manner as above, and these were confirmed to have the same neurite formation promoting effect like that of L-valine (FIG. 4).

Figure 5:
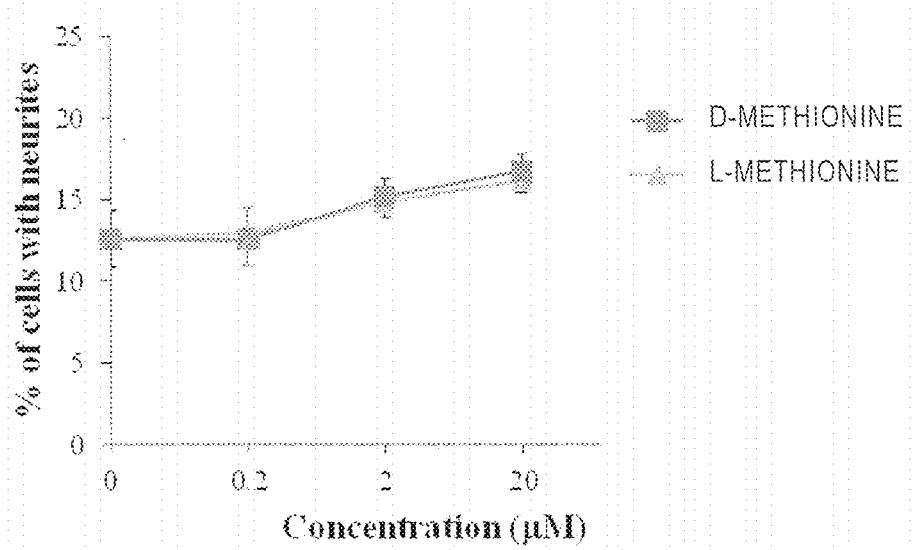
FIG. 5 This is a graph showing a neurite formation rate in cultivation of Bt$_2$cAMP-added PC12 cells in an RPMI-1640 medium added with an L-methionine solution or a D-methionine solution in an amount of 0.2 μM, 2 μM or 20 μM.

Further, other amino acids than branched chain amino acids were checked for the $Bt_2cAMP$-inductive neurite formation effect thereof in the same manner as above. As a result, aspartic acid, glutamic acid, cysteine, tryptophan, phenylalanine, tyrosine, serine, threonine, asparagine, glutamine, arginine, lysine, histidine, glycine, alanine and proline could not provide any significant change in the neurite formation ratio even when the concentration of each amino acid added to the RPMI-1640 medium was increased up to 200 μM. On the other hand, the system where L-methionine or D-methionine was added to the medium at a high concentration of 20 μM exhibited the neurite formation promoting effect (FIG. 5).

Next, co-addition of valine and methionine to a medium was checked for the effect. In the same manner as above, $Bt_2cAMP$ was added to an RPMI-1640 medium where PC12 cells were sown and cultivated in each well, and further, an L-valine solution, an L-methionine solution, or a solution of a mixture prepared by mixing L-valine and L-methionine at 1/1 was added thereto and the cells were further cultivated to check for the neurite formation rate. Regarding the concentration of the amino acid added to the RPMI-1640 medium, the concentration in the system using the L-valine solution or the L-methionine solution was 0.2 μM, and the concentration of L-valine and L-methionine in the system using the L-valine and L-methionine mixture solution was 0.1 μM each, totaling 0.2 μM. The measured data of the neurite formation rate are shown in FIG. 6.

Figure 6:
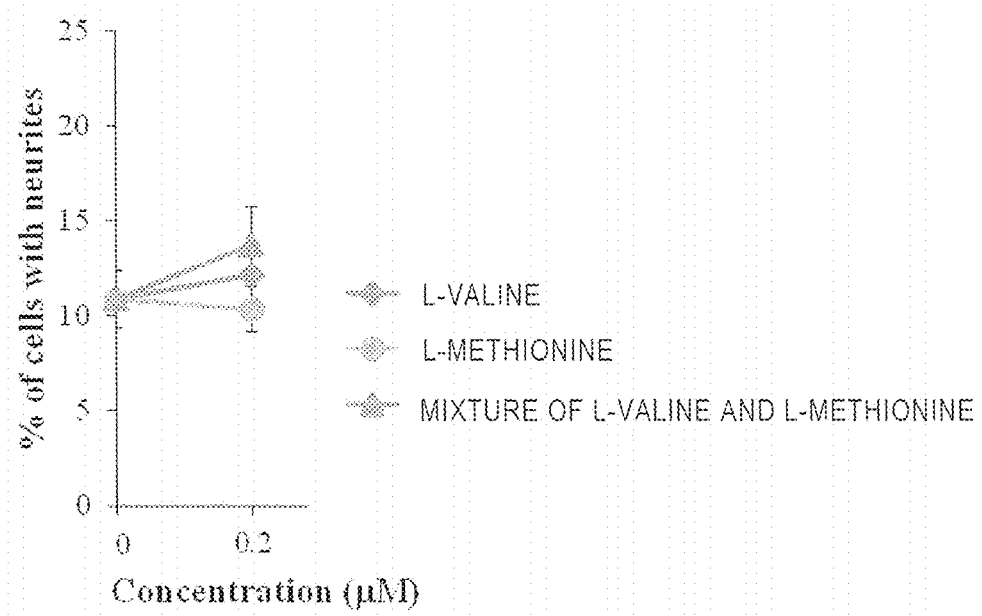
FIG. 6 This is a graph showing a neurite formation rate in cultivation of Bt$_2$cAMP-added PC12 cells in an RPMI-1640 medium added with an L-valine solution, an L-methionine solution and a solution of a mixture of L-valine and L-methionine in an amount of 0.2 μM.

As shown in FIG. 6, co-addition of L-valine and L-methionine to the medium exhibited a higher neurite formation promoting effect an that in the case where each amino acid was added singly to the system. This indicates that co-addition of valine and methionine results in synergistic improvement in the neurite formation promoting effect. In addition, it is also known that in the case of co-addition of valine and methionine, a combination of an unsubstituted valine and an unsubstituted methionine is preferred in point of enhancing the effect.

(c) Evaluation of Effect for NGF-Inductive Neural Differentiation

A neurofilament was used as a neural differentiation marker. This was stained according to an immunofluorescent staining method for evaluating the neural differentiation promoting effect of L-valine.

PC12 cells were floated in a basal medium and well suspended therein to be single cells of $1.4 \times 10^4$ cells/mL. The suspension of PC12 cells was sown in a collagen-coated 8-well chamber slide at $5.0 \times 10^3$ cells/360 μL/well, and cultivated in a 5% $CO_2$ vapor phase in an incubator at 37° C. for 24 hours. After the cultivation, Dulbecco PBS(−) containing 200 ng/mL of NGF (NGF solution), and an RPMI-1640 medium containing 4 μg/mL of L-valine (L-valine solution prepared in Preparation Example 1) were added to each well in an amount of 20 μL each, and the cells were further cultivated for 48 hours. After the cultivation, the medium as removed from each well, the wells were washed with PBS(−) (phosphate buffered saline (free from Ca and Mg)), and then a 4% formaldehyde solution was added to each well and treated for 30 minutes, and thereafter each well was washed three times with PBS(−). Subsequently, PBS(−) containing 0.4% Triton X-100 (manufactured by Sigma Aldrich Corporation) was added to each well and treated for 30 minutes, and then the wells were washed with PBS(−).

Next, PBS(−) containing 2.5% bovine serum albumin (BSA) was added to each well and treated for 1 hour, then a primary antibody (Anti-neurofilament 200 IgG fraction of antiserum; manufactured by Sigma Aldrich Corporation) diluted by 200 times with PBS(−) containing 2.5% BSA was added to each well and treated at room temperature for 2 hours, and washed three times with PBS(−) containing 0.05% Tween 20 (manufactured by ATTO Corporation) for 3 minutes. Subsequently, a secondary antibody (Anti-Rabbit IgG (whole molecule)-FITC antibody produced in goat; manufactured by Sigma Aldrich Corporation) diluted by 200 times with PBS(−) containing 2.5% BSA was added to each well and treated at room temperature for 1 hour, and washed three times with PBS(−) containing 0.05% Tween 20 for 3 minutes. The sample in each well treated in the manner as above was sealed up with a nuclear stain sealant (DAPI-Fluoromount-G, manufactured by Cosmo Bio Corporation), covered with a cover glass, and the four sides thereof were manicured to produce a sample 1. On the other hand, a comparative sample 1 was produced according to the same process of cultivation and immunofluorescent staining as above, except that Dulbecco PBS(−) was used in place of the NGF solution and an RPMI-1640 medium was used in place of the L-valine solution; and a comparative sample 2 was produced according to the same process of cultivation and immunofluorescent staining as above, except that an RPMI-1640 medium was used in place of the L-valine solution.

Figure 7:
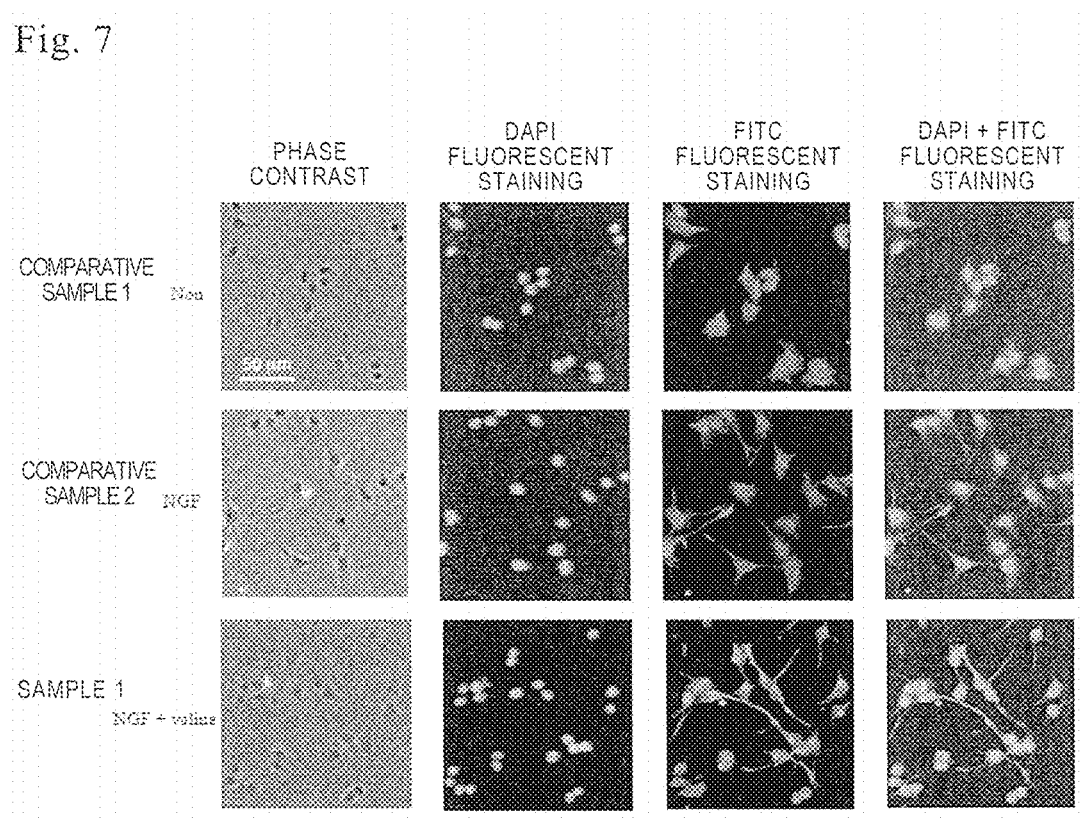
FIG. 7 This shows phase-contrast photographs and fluorescently stained images of PC12 cells cultivated with no addition of NGF and L-valine to the medium (comparative sample 1), PC12 cells cultivated with addition of NGF to the medium (comparative sample 2) and PC12 cells cultivated with addition of NGF and L-valine to the medium (sample 1).

A fluorescently-stained image of each sample was observed and picture thereof was taken using a confocal laser microscope (FLUOVIEWFV10i, manufactured by Olympus Corporation). The pictures are shown in FIG. 7. In FIG. 7, the pictures in the first vertical row from the left are phase contrast pictures of samples. The pictures in the second vertical row from the left are DAPI fluorescently-stained images taken at an excitation wavelength of 359 nm and a detection wavelength of 461 nm, in which the bright spots correspond to nuclei. The pictures in the third vertical row from the left are FITC fluorescently-stained images taken at an excitation wavelength of 495 nm and a detection wavelength of 519 nm, in which the bright spots correspond to neurofilaments. The pictures in the fourth vertical row from the left are composite pictures or the second row pictures and the third row pictures from the left.

The FITC fluorescently-stained image of the sample 1 where NGF and L-valine were added to the medium is compared with that of the comparative sample 2 where NGF was added to the medium but L-valine was not added thereto. It is known that fluorescently-stained image of the sample 1 has a larger number of bright spots than those in the fluorescently-stained image of the comparative sample 2, that is, a larger number of neurofilaments appeared in the former. From this, it is known that adding a valine to a medium promotes neural differentiation from stem cells.

INDUSTRIAL APPLICABILITY

According to the present invention, there can be provided a nerve growth promoter at low cost, which can effectively promote differentiation of stem cells into nerve cells and formation of neurites in nerve cells, and in which the active ingredient is hardly degraded by digestive enzymes. Consequently, using the nerve growth promoter of the present invention, there can be provided an inexpensive internal agent that can relive cognitive dysfunction and motor dysfunction to be caused by neurodegenerative disorders or nerve damages. Accordingly, the industrial applicability of the present invention is great.

The invention claimed is:

1. A method for promoting nerve growth, comprising administering to an animal an effective amount of valine or a substituted valine in which a hydrogen atom of the amino group of valine is substituted with an alkyl group or an acyl group, wherein the only active ingredient administered is valine or the substituted valine.

2. A method for promoting nerve growth comprising administering to an animal an effective amount of valine or a substituted valine in which a hydrogen atom of the amino group of valine is substituted with an alkyl group or an acyl group, in combination with methionine or a substituted methionine in which a hydrogen atom of the amino group of methionine is substituted with an alkyl group or an acyl group.

3. The method according to claim 1, wherein the only amino acid administered is valine.

4. The method according to claim 2, wherein the only amino acids administered are valine and methionine.

5. The method according to claim 2, wherein the only active ingredients administered are valine and methionine.

6. The method according to claim 1, which is for promoting differentiation of stem cells into nerve cells.

7. The method according to claim 2, which is for promoting differentiation of stem cells into nerve cells.

8. The method according to claim 1, which is for forming neurites in nerve cells.

9. The method according to claim 2, which is for forming neurites in nerve cells.

10. The method according to claim 1, which is for promoting formation of neurites induced by dibutyryl cAMP.

11. The method according to claim 2, which is for promoting formation of neurites induced by dibutyryl cAMP.

12. The method according to claim 1, which is for promoting neural differentiation induced by a nerve growth factor.

13. The method according to claim 2, which is for promoting neural differentiation induced by a nerve growth factor.

14. The method according to claim 1, which is for relieving damages of motor function.

15. The method according to claim 2, which is for relieving damages of motor function.

16. A method for promoting nerve growth comprising administering to an animal an effective amount of valine or a substituted valine in which a hydrogen atom of the amino group of valine is substituted with an alkyl group or an acyl group, which is
   for promoting differentiation of stem cells into nerve cells,
   for forming neurites in nerve cells, or
   for promoting formation of neurites induced by dibutyryl cAMP.

17. The method according to claim 16, which is for promoting differentiation of stem cells into nerve cells.

18. The method according to claim 16, which is for forming neurites in nerve cells.

19. The method according to claim 16, which is for promoting formation of neurites induced by dibutyryl cAMP.

* * * * *